(12) United States Patent
Wright et al.

(10) Patent No.: US 12,290,938 B2
(45) Date of Patent: May 6, 2025

(54) ROBOTIC ARM SYSTEM, METHOD AND COMPUTER PROGRAM

(71) Applicant: Sony Group Corporation, Tokyo (JP)

(72) Inventors: Christopher Wright, London (GB); Bernadette Elliott-Bowman, London (GB); Naoyuki Hirota, Tokyo (JP)

(73) Assignee: Sony Group Corporation, Tokyo (JP)

( * ) Notice: Subject to any disclaimer, the term of this patent is extended or adjusted under 35 U.S.C. 154(b) by 298 days.

(21) Appl. No.: 17/784,125

(22) PCT Filed: Dec. 11, 2020

(86) PCT No.: PCT/JP2020/046432
§ 371 (c)(1),
(2) Date: Jun. 10, 2022

(87) PCT Pub. No.: WO2021/125115
PCT Pub. Date: Jun. 24, 2021

(65) Prior Publication Data
US 2023/0029184 A1    Jan. 26, 2023

(30) Foreign Application Priority Data

Dec. 19, 2019   (EP) ..................... 19218114

(51) Int. Cl.
*B25J 9/16*   (2006.01)
*A61B 17/00*   (2006.01)
(Continued)

(52) U.S. Cl.
CPC ............. *B25J 9/1676* (2013.01); *A61B 34/25* (2016.02); *A61B 34/37* (2016.02); *G06F 3/017* (2013.01);
(Continued)

(58) Field of Classification Search
CPC .......... A61B 2017/00207; A61B 34/20; A61B 34/25; A61B 34/30; A61B 34/37;
(Continued)

(56) References Cited

U.S. PATENT DOCUMENTS

2016/0338782 A1* 11/2016 Bowling ............ A61B 17/1675
2018/0036884 A1*  2/2018 Chen ..................... B25J 9/1676
(Continued)

FOREIGN PATENT DOCUMENTS

JP   2010-200894 A       9/2010
KR   20180015228 A  *  2/2018  ............... G06F 3/01
(Continued)

OTHER PUBLICATIONS

International Search Report and Written Opinion mailed on Mar. 22, 2021, received for PCT Application PCT/JP2020/046432, filed on Dec. 11, 2020, 12 pages.

*Primary Examiner* — Adam R Mott
*Assistant Examiner* — James Miller Watts, III
(74) *Attorney, Agent, or Firm* — XSENSUS LLP

(57) ABSTRACT

A robotic arm system for surgery is described. The method includes: processing circuitry configured to: apply a virtual barrier preventing a human controlled surgical device from entering an area within a surgical scene; and release the virtual barrier in response to a gesture.

11 Claims, 11 Drawing Sheets

(51) Int. Cl.
  *A61B 34/00*   (2016.01)
  *A61B 34/37*   (2016.01)
  *G06F 3/01*    (2006.01)

(52) U.S. Cl.
  CPC ............ *A61B 2017/00207* (2013.01); *G05B 2219/36454* (2013.01); *G05B 2219/39001* (2013.01)

(58) Field of Classification Search
  CPC ......... B25J 9/1676; G05B 2219/36454; G05B 2219/39001; G06F 3/017; G06F 3/048; G06F 3/0487; G06F 3/0488; G06F 3/04883
  See application file for complete search history.

(56) References Cited

U.S. PATENT DOCUMENTS

| | | | |
|---|---|---|---|
| 2019/0183591 A1* | 6/2019 | Johnson | B25J 9/1666 |
| 2019/0282310 A1 | 9/2019 | Beelen et al. | |
| 2020/0188026 A1* | 6/2020 | de Souza | A61B 34/10 |
| 2021/0038335 A1* | 2/2021 | Maret | A61B 34/74 |

FOREIGN PATENT DOCUMENTS

| | | | | |
|---|---|---|---|---|
| WO | 2016/187290 A1 | 11/2016 | | |
| WO | WO-2018089923 A1 * | 5/2018 | ............ | A61B 18/02 |
| WO | WO-2018159328 A1 * | 9/2018 | ......... | A61B 1/00149 |

* cited by examiner

| Surgical Step | Anatomical Parts in Surgical Scene | | Anatomical Parts to Access | Surgical Tool | Gesture |
|---|---|---|---|---|---|
| Incision | Body | | Stomach Area | Scalpel | Vertical movement 3mm cutting depth |
| | Stomach Area | | | | |
| Expose Stomach | ...... | | ...... | ...... | ...... |
| Remove Tumour | Tumour | | Tumour, Stomach | Forceps, Scalpel | Forceps - grip, 40° rotation |
| | Stomach | | | | |
| | Body | | | | Scalpel - diagonal movement 5mm cutting depth |
| | Spine | | | | |
| | Intestinal Tract | | | | |
| Repair Patient | ...... | | | | |

ROBOTIC ARM SYSTEM, METHOD AND COMPUTER PROGRAM

CROSS-REFERENCE TO RELATED APPLICATIONS

The present application is based on PCT filing PCT/JP2020/046432, filed Dec. 11, 2020, which claims priority to EP 19218114.7, filed Dec. 19, 2019, the entire contents of each are incorporated herein by reference.

FIELD

The present technique relates to a robotic arm system, method and computer program.

BACKGROUND

The "background" description provided herein is for the purpose of generally presenting the context of the disclosure. Work of the presently named inventors, to the extent it is described in the background section, as well as aspects of the description which may not otherwise qualify as prior art at the time of filing, are neither expressly or impliedly admitted as prior art against the present technique.

Surgeons are increasingly performing surgery using robotic assistance. In particular, so-called "master-slave" devices are being increasingly used in surgery. These types of devices have a surgeon control a number of robotic arms to perform the surgery on a patient.

Whilst these devices have many benefits, it is possible for the human surgeon controlling the robotic to accidentally move the robotic arm into the patient. In other words, the surgeon may inadvertently move the robotic arm when performing a particularly delicate part of the surgery. This can cause injury to the patient. Moreover, with complex surgery, fatigue of the human surgeon may reduce the dexterity with which the human surgeon controls the robotic arms. This again may increase the risk of accidental movement of the robotic arm into the patient which may cause injury to the patient.

It is an aim of the present disclosure to at least address one or more of these issues.

SUMMARY

According to embodiments of the disclosure, a robotic arm system for surgery, including: processing circuitry configured to: apply a virtual barrier preventing a human controlled surgical device from entering an area within a surgical scene; and release the virtual barrier in response to a gesture.

Features of the disclosure are provided in the appended claims.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF DRAWINGS

A more complete appreciation of the disclosure and many of the attendant advantages thereof will be readily obtained as the same becomes better understood by reference to the following detailed description when considered in connection with the accompanying drawings.

FIG. 3 shows a data structure 1050 according to embodiments.

DESCRIPTION OF EMBODIMENTS

Figure 1:
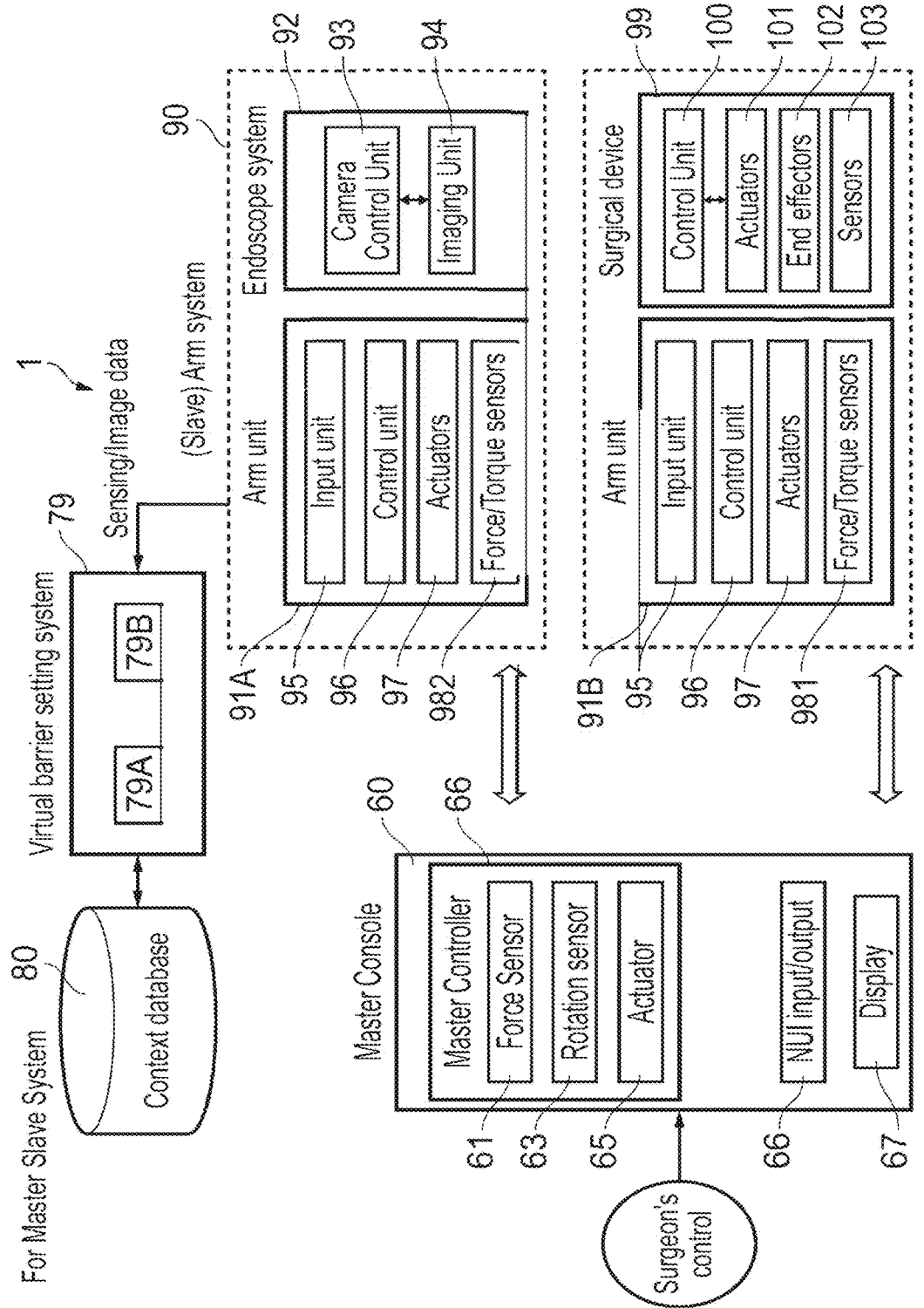
FIG. 1 shows a medical robot system 1 according to embodiments of the present disclosure.

Referring now to the drawings, wherein like reference numerals designate identical or corresponding parts throughout the several views.

With reference to FIG. 1, a configuration example of a medical robot system using a virtual barrier according to an embodiment of the present disclosure is applicable will be described. A medical robot system 1 illustrated in FIG. 1 is a master-slave medical robot system. In the medical robot system 1, a user operates a master apparatus 60 to transmit an operation command to a slave apparatus 90 through a wired or wireless communication means and remotely operate the slave apparatus 90. The slave apparatus 90 in this Figure has two robotic arms in an arm system 90; a first arm unit 91A operates an endoscope system 92 and a second arm unit 91B operates a surgical device such as a cauterizer 99. Of course, the disclosure is not so limited and the arm system 90 may include any number of arm units. Moreover, each arm unit may control one or more surgical device.

As would be appreciated, the endoscope system 92 located on the first arm unit 91A includes a camera control unit 93 and an imaging unit 94. The camera control unit 93 controls the imaging unit 94 to capture an image of a surgical site. For example, the camera control unit 93 controls the focus of the imaging unit 94 and the lighting of the surgical site to ensure that the image captured by the imaging unit 94 is correct. The captured image is sent to a display located on the master apparatus 60 that is viewed by the surgeon.

Further, the captured image is sent to a virtual barrier setting system 79 which will be described later.

The cauterizer 99 on the second arm unit 91B is controlled by a control unit 100. The control unit 100 receives instructions from a master controller 66 within the master apparatus 60. The control unit 100 controls actuators 101 within the cauterizer 99 to move the cauterizer 99 to the correct position on the surgical site. In this case, the actuators 101 move an end effector 102 to a position on the surgical site where a wound is to be cauterized. The cauterization will be performed by the end effector 102. In order for the virtual barrier setting system 79 to know the location of the cauterizer 99, sensors 103 are located on the cauterizer 99. These sensors 103 may measure the axial and radial movement of the cauterizer 99.

The virtual barrier according to the present embodiment limits the movement of the slave apparatus 90 to avoid injury to the patient. The virtual barrier is set by a virtual barrier setting system 79. Therefore, embodiments of the disclosure are performed by the virtual barrier setting system 79. The control apparatus 79 contains processing circuitry 79A which is controlled by software. The software may be stored within storage 79B on the control apparatus 79 or may be controlled using software stored over a network (the control apparatus accessing the network and thus the software).

FIG. 1 illustrates that the medical robot system 1 includes the slave apparatus 90, the master apparatus 60, the virtual barrier setting system 79 and a context database 80. As will be explained later, the context database 80 stores information relating to the surgical procedure currently being undertaken to allow the virtual barrier setting system 79 to set up and remove an appropriate virtual barrier during a surgical procedure.

The master apparatus 60 drives the slave apparatus 90 in accordance with an instruction input from the human surgeon. The control apparatus 79 also controls the virtual barriers according to embodiments applied at the slave apparatus 90 as will be explained later.

Note that the block diagram illustrated in FIG. 1 illustrates only components that are necessary in particular to describe the present disclosure. The medical robot system 1 may also include a variety of components included in a general master-slave medical robot system in addition to the illustrated components.

The medical robot system 1 has information transmission systems roughly divided into a system for performing drive control over the slave apparatus 90 and providing virtual barriers to restrict the movement of the slave apparatus 90 to various body until certain unlock movements have been provided. The following simply describes the medical robot system 1 for each of the information transmission systems.

First, the system for performing drive control over the slave apparatus 90 will be described. In drive control over the slave apparatus 90, a surgeon operates the operation portion attached to the front end of the arm of the master apparatus 60 to transmit information indicating an instruction to drive the arm of the slave apparatus 90 from the master apparatus 60. In the case where the surgical instrument includes a drivable section, information indicating an instruction to drive the surgical instrument can also be transmitted together from the master apparatus 60 to the control apparatus 79. In the present embodiment, the master apparatus 60 includes a grasping-type operation portion. The configuration of the operation portion will be described below in detail.

The master apparatus 60 includes a force sensor (torque sensor) 61, a rotation angle sensor 63, and an actuator 65 as components for performing drive control over the slave apparatus 90. The force sensor 61 is provided, for example, to a connected part between the arm and the operation portion attached to the front end of the arm, and detects force acting in the directions of three axes orthogonal to each other. That is, the force sensor 61 detects force input by a surgeon to the operation portion. In addition, the rotation angle sensors 63 are provided to a plurality of joint portions of the arm, and detect the rotation angles of the respective joint portions. The rotation angle sensor 63 may be, for example, an encoder.

The master apparatus 60 also includes a display 67 that allows the surgeon to see the surgical site being accessed by the slave system 90. Further, the virtual barrier setting system 79 may also include an overlay on the displayed image identifying the location of one or more virtual barriers defined by the virtual barrier setting system 79 as will be explained later. The surgeon may also interact with the image or various controls provided on the display using a user interface 66. Although a touch screen is noted as one example of a user control, the disclosure is not so limited and a joystick or mouse, buttons, trackpad or other kind of interface is envisaged.

The master apparatus 60 performs a variety of arithmetic operations related to drive control over the slave apparatus 90 on the basis of information input from the force sensor 61 and the rotation angle sensor 63. This is performed within a master controller 66. For example, the master controller 66 calculates torque to be generated in each actuator 97 of the arm of the slave apparatus 90 on the basis of force acting on the operation portion which is detected by the force sensor 61 in the case where force control is used to perform drive control over the slave apparatus 90. In addition, the master controller 66 calculates the target value of the rotation angle of each joint portion of the arm of the slave apparatus 90 on the basis of the rotation angle of each joint portion of the arm which is detected by the rotation angle sensor 63 in the case where position control is used to perform drive control over the slave apparatus 90. In addition, in the case where the surgical instrument of the slave apparatus 90 includes a drivable section, the amount of control for driving the surgical instrument can be calculated by the master controller 66.

In the present embodiment, as a scheme of drive control over the slave apparatus 90, a variety of publicly known control systems may be used. As the master apparatus 60, what is adapted to an adopted control system can be constructed as appropriate. The specific configuration of the master apparatus 60 may be similar to existing configurations corresponding to a variety of control systems, so that it will not be described in detail.

As noted above, the slave apparatus 90 includes one or more arm units 91A and 91B.

Each arm unit includes a force sensor (torque sensor) 98, an actuator 97 as components used to perform drive control over the arm and present haptic sensation. A driving signal corresponding to the amount of control calculated by the master controller 66 is transmitted to the actuator 97 of the appropriate arm unit 91A and 91B. The actuators 97 are provided, for example, to the plurality of joint portions of the arm, and rotate and drive the respective joint portions. The actuator 97 may be, for example, a servo motor. The actuator 97 is driven in accordance with the amount of control calculated by the master apparatus 60, thereby operating the arm as instructed by a surgeon. In addition, in the case where the surgical instrument includes a drivable section, the master apparatus 60 can transmit a driving signal for a motor for operating the drivable section. The motor is driven in accordance with the amount of control calculated by the master apparatus 60, thereby operating the surgical instrument as instructed by a surgeon.

Moreover, the force sensor 981 and 982 and the rotation angle sensor determine the amount of movement of the robotic arm(s) and any surgical tools attached thereto.

The force sensor 981 and 982 detects external force acting on a surgical instrument. The force sensors 981 and 982 are provided, for example, to the plurality of joint portions of the arm, and detect force (torque) acting on the respective joint portions. For example, the rotation angle sensors are provided to a plurality of joint portions of the arm, and detect the rotation angles of the respective joint portions. The rotation angle sensor 93 may be, for example, an encoder. The information detected by these force sensors 98 and rotation angle sensors is transmitted to the master apparatus 60. The master controller 66 consecutively grasps the current state of the arm on the basis of the information, and calculates the amount of control described above by taking even the current state of the arm into consideration.

In addition, the information detected by the force sensors 98 and the rotation angle sensors are provided to the virtual barrier setting system 79. The virtual barrier setting system 79 identifies the movement that is being applied to each arm unit 91A and 91B by the master controller 66 and determines whether the application of the movement would breach the virtual barriers defined by the virtual barrier setting system 79.

In the event that the movement being applied to each arm unit 91A and 91B breaches the defined virtual barriers, the virtual barrier setting system 79 controls the actuator 97 in the respective arm unit 91A and 91B to stop moving. The respective arm unit 91A and 91B can inform the master controller 66 that the virtual barrier setting system 79 has stopped the movement. This feedback may then be provided to the surgeon. Of course, the virtual barrier setting system 79 may directly inform the master controller 66 that the movement of the respective arm unit 91A and 91B has been stopped by the virtual barrier setting system 79.

The feedback may be displayed on a display unit 67 located within the master apparatus 60.

Here, force acting on the surgical instrument attached to the front end of the arm can be reflected in force acting on each joint portion which is detected by the force sensor 981 and 982. The master controller 66 extracts a component of the force acting on the surgical instrument from the force acting on each joint portion which is detected by the force sensor 981 and 982, and calculates the amount of control over the actuator 65 of the master apparatus 60. The actuator 65 may be, for example, a servo motor. The master controller 66 drives the arm in accordance with the force acting on the surgical instrument to impart, for example, resistance to an operation input by a surgeon to the operation portion, thereby presenting the force acting on the surgical instrument to the surgeon. The medical robot system 1 has functions of detecting force acting on a surgical instrument, and, if appropriate, feeding the force back to a surgeon.

Embodiments of the present disclosure will now be explained with reference to FIGS. 2 to 9. In particular, embodiments of the present disclosure will be described with reference to a surgical procedure to remove a tumour from a patient's stomach. Of course, the disclosure is not so limited and the disclosure can be applied to any surgical procedure. For example, the disclosure can be applied to any procedure using a surgical instrument. Examples of a procedure may include a procedure performed by an endoscope (for example as laparoscope), an exoscope, a surgical microscope or the like. As would be apparent, the disclosure can be applied to any surgical procedure where access of the robot arm to part of the surgical site is to be restricted.

Figure 2:
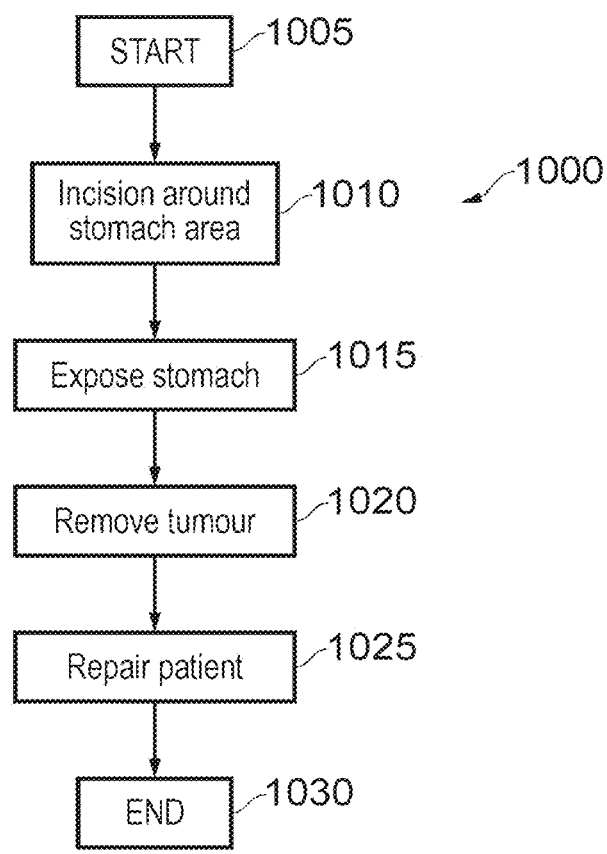
FIG. 2 shows a surgical procedure plan 1000 according to embodiment.

Referring to FIG. 2, a flow chart 1000 describing a surgical plan is shown. This surgical plan describes the general process of stomach surgery to remove a cancerous tumour on a patient's stomach. Of course, any surgical procedure is envisaged and an appropriate surgical plan would be produced for the surgical procedure.

The process 1000 starts at step 1005. The process moves to step 1010 where the surgeon will control the human controlled surgical device (hereinafter referred to as a "surgical device") such as a scalpel held by the slave apparatus 90 in the medical robot system 1 to perform an incision around the stomach area. In particular, the scalpel is one example of a surgical device that may be held by one of the arm units described with reference to FIG. 1. Of course, in some instances, the arm unit itself will move without a tool being held by the arm unit. In this case, the arm unit itself will be the surgical device. As will be appreciated, in order to perform an incision, a scalpel or some other cutting tool will be required to be attached to an arm on the surgical device.

After an incision has been made, the process moves to step 1015 where the patient's stomach is exposed. In other words, after the incision is made through the skin, the surgical device is controlled by the surgeon to peel back the skin layer of the abdomen and a further incision is made in the fascia tissue. This is again peeled back to expose the stomach having the cancerous tumour.

During the incision, care has to be taken to avoid causing unnecessary trauma to the patient and to avoid cutting any one of the many blood vessels that travel through the abdomen such as the aorta, the inferior vena cava or any of their many branches.

Moreover, around the stomach, other important organs and tissue exists such as the spine, liver and intestinal tract. These organs, tissue and blood vessels are not part of the surgery and, whilst in the surgical scene due to their proximity to the stomach, are not to be touched by the surgical device to avoid causing unnecessary trauma. In other words, although the surgeon controlling the surgical device may see or be at least adjacent to these organs, tissue, and blood vessels and so they are in the surgical scene, the surgical device should avoid contact with these organs and tissue.

Accordingly, as will be explained later, a virtual barrier is placed around areas within the surgical scene that are not to be touched by the surgical device controlled by the surgeon. These areas may be organs, or parts of organs, tissue within a patient, veins, arteries or other areas of the patient which are not part of the surgical procedure but which may be part of the surgical scene. The virtual barrier is therefore an exclusion zone which physically cannot be entered by the surgical device held by the slave apparatus 90.

After the stomach is exposed in step 1015, the surgical procedure moves to step 1020 where the tumour is removed. This requires the surgeon to control the surgical device to cut out or otherwise excise the tumour from the stomach.

After the tumour has been removed in step 1020, the process moves to step 1025 where the patient is repaired. In other words, the surgeon controlling the surgical device will close the fascia tissue and apply a suture along the wound. The surgeon controlling the surgical device will then close the skin and apply a suture along that wound.

The surgery then ends in step 1030.

During the creation of the surgical plan explained with reference to FIG. 2, a data structure 1050 is populated. An example of the data structure 1050 is shown in FIG. 3. The data structure 1050 in FIG. 3 is a database, although this is exemplary. The data structure 1050 is stored within the control apparatus 79.

In the data structure 1050, the four different steps associated with the surgical plan are shown in the column entitled "Surgical Step". In particular, the incision step, the expose stomach step, the remove tumour step and the repair patient step. For brevity, only two of these steps (the incision step and the remove tumour step) will be described in detail.

Associated with each of these steps are the anatomical parts which will be located in the surgical scene, the anatomical parts which the surgical device will need to access, the surgical tool required to act upon the accessed anatomical part and a test which the human surgeon, when controlling the surgical device mounted on the slave apparatus 90 will need to pass in order to gain access to the anatomical part. These will be defined during the surgical planning phase and may be based purely on the knowledge of the surgeon or may be selected from previously performed similar surgical procedures or the like.

In the embodiments of FIG. 3, the anatomical parts in the surgical scene associated with the incision are the body of the patient and the stomach area. Although the embodiments of FIG. 3 show these parts in a list, the disclosure is not so limited. For example, an image of a patient's body may be used to assist in identifying the body in the surgical scene. Additionally, the stomach area where the surgical device will perform the incision may be marked on the patient when the image of the patient's body is captured. This means that the human surgeon will be able to precisely define the boundary of the virtual barriers during the surgery planning phase.

The anatomical parts requiring access are also associated with the incision step of the surgical procedure. In embodiments, the stomach area is the part to access during the incision step as would be appreciated. Again, the human surgeon may define this, or this may be established from previous surgical procedures of this type.

The surgical tool or tools (the surgical device) which are used to perform the incision surgical step are also associated with the surgical step. In this case, a scalpel will be used to perform the incision step.

Finally, a gesture which the human surgeon controlling the surgical device mounted on the slave apparatus 90 must perform in order to remove the virtual barrier to access the anatomical part associated with the incision surgical step is defined. In embodiments, the gesture is performed within the surgical scene. For example, the human surgeon controlling the slave apparatus 90 demonstrates a gesture that is related to the surgical action they will perform in the next surgical step. However, the disclosure is not so limited and the gesture may be a voice command instructing the virtual barrier to drop. This voice command may be issued in the case of a deteriorating patient condition or because the human surgeon confirms they are ready to perform the next surgical procedure.

In embodiments, the gesture may be performed by the surgical device mounted on the slave apparatus 90 under the control of the human surgeon. In these embodiments, the gesture may be associated with the movement of the surgical tool required in the next surgical step. So, in the example of the removal of the virtual barrier to allow the surgical tool access to the stomach area to perform an incision, the surgical tool (the scalpel) will have to perform a vertical movement of 3 mm cutting depth. This is the movement of the surgical tool required to perform the incision. Therefore, the surgical device will have to perform a vertical movement of 3 mm of the scalpel within the surgical scene to remove the virtual barrier to permit access to the patient's stomach area. In embodiments, the surgical device will move the scalpel above the patient, although the disclosure is not so limited. For example the vertical movement may occur next to the patient or in a designated area around the slave apparatus 90. The force sensor 91 and the rotation angle sensor 93 within the slave apparatus 90 will be used to determine the movement of the surgical device and the results of the movement will be provided to the control apparatus 79 to determine if the surgeon has passed the gesture control. In the event of passing the gesture control, the virtual barrier within the surgical scene will be removed to allow the surgical device to access the anatomical part.

In other instances, the gesture may be the opening and/or closing of the human controlled surgical device. This may be appropriate where the surgical device is a pair of surgical scissors, forceps or the like.

In yet other instances, the gesture may be a movement of a pattern on the virtual barrier. In other words, the surgeon may control the surgical device to move the surgical device on the virtual barrier in a particular manner so that a pattern is followed. This tests the surgeon's skill with the surgical device and thus improves safety for the patient. One example pattern is a plurality of taps on the virtual barrier. This pattern is quick and indicates that the surgeon is ready to release the virtual barrier. In examples, the pattern is a movement of a trajectory across the surface of the virtual barrier. In other words, the surgeon moves the surgical device is a particular manner across the surface of the virtual barrier. This again tests the surgeon's skill.

In embodiments, the gesture may be a hand gesture or voice command, or a combination of the hand gesture and the voice command. For example, the human surgeon may move his or her hand in a manner indicating the type of action required on the anatomical part. So, for example, the human surgeon may make a hand gesture indicative of an incision or may say "perform incision on stomach" to indicate to the control apparatus 79 that the human surgeon is ready to perform the next surgical step. In the event that the next surgical step is correctly noted by the human surgeon, the virtual barrier associated with the next surgical step will be removed. The gesture may be detected by a camera or microphone located in the operating theatre. Although this example is an incision on the stomach, the disclosure is in no way limited to this and the surgical procedure may be one of cautery, ligature, extraction or puncture.

In some instances, the gesture pattern is related to a particular structure located in the surgical site that is protected by the virtual barrier. For example, if the virtual barrier protects the stomach, the gesture pattern may require the surgical device to trace around the stomach. This again tests the dexterity and skill of the surgeon. The structure may also be an anatomical structure such as bone, tissue or an artery or the like.

Although the gesture is described as removing the virtual barrier to allow access to the anatomical part for the next surgical step, the disclosure is not so limited. For example, if the human surgeon needs emergency access to a part of the patient that is subject to a virtual barrier, the human surgeon may issue a special voice command or hand gesture that removes one or more of the virtual barriers to allow the surgical device immediate access. This may be useful in a surgical procedure where a patient's condition (i.e. their wellbeing) deteriorates rapidly and the human surgeon needs to take urgent remedial action using the surgical device. Of course, the disclosure is not so limited.

By ensuring that the surgeon can control the surgical tool held by the slave apparatus 90 in this way, the ability of the surgeon to perform the next surgical task is tested prior to the surgeon performing the surgical task on the patient using the slave apparatus 90. This increases safety for the patient as the skill levels of the surgeon for the surgical task and the fatigue levels of the surgeon are tested before they can attempt to perform the surgical task. Moreover, this increase of safety is also achieved by the human surgeon indicating using either one or more hand gesture or voice command the next surgical step. This is because the virtual barrier will only be removed if the human surgeon indicates the correct next surgical step.

As noted above, the vertical movement may be determined using the force sensor 91A or 91B and/or the rotation sensor as would be appreciated. However, other mechanisms of determining the vertical movement are envisaged such as a time of flight sensor located on the slave apparatus 90, or from the image captured of the surgical scene. Other suitable sensors include an image sensor or a multispectral sensor.

In embodiments, the position of the surgical tool mounted on the slave apparatus 90 may also determine the gesture. In this embodiment, the gesture is selected based on the starting position of the human controlled surgical device of the surgical procedure next being performed. In other words, the gesture may also ensure that the surgical tool is in the correct position on the patient for the surgical procedure next being performed. This improves the speed of the surgical procedure and reduces the risk of injury to the patient.

In embodiments, the virtual barrier is removed in dependence upon the tool (for example the type of surgical device) on the slave apparatus 90. This means, for example, that the surgical tool held by the slave apparatus 90 is determined. The surgical tool held by the slave apparatus 90 is compared with the surgical tool or tools required to perform the next surgical procedure (which is noted in the "surgical tool" column of the data structure 1050) and if the surgical tool is not the same as that noted in the "surgical tool" column, the virtual barrier will not be removed. So, for example, if the only surgical tool held by the surgical device is a cauteriser and the surgical procedure next being performed is an incision (where a scalpel should be used), the virtual barrier around the stomach area will not be removed even if the human surgeon controls the slave apparatus 90 to perform the gesture defined in the data structure 1050. This reduces the risk of injury to the patient.

In embodiments, the type of surgical tool held by the slave apparatus 90 may be determined by image recognition of the surgical scene. For example, the slave apparatus 90 may recognise an image of a scalpel entering the surgical scene. Alternatively or additionally, the user may interact with the slave apparatus 90 to indicate the type of surgical tool held by the slave apparatus 90. This may be via voice command such as "connecting scalpel to slave apparatus" or may be via a touch screen or gaze control or the like. Moreover, the surgical tool may have a unique identifier associated with it. The unique identifier may include information identifying the type of surgical tool which may be automatically recognized by the slave apparatus 90. This unique identifier may be communicated to the slave apparatus 90 using wireless communication, or a QR code or the like.

As would be appreciated, the above gesture mechanisms for removing the virtual barrier may be used together or separately. In other words, the human surgeon may need to perform a hand gesture and issue a voice command in order to remove the virtual barrier. This further improves the safety of the patient as the likelihood of accidentally removing the virtual barrier is reduced.

Referring back to FIG. 3, although not shown for brevity, similar information would be included in the data structure 1050 for the "Expose Stomach" surgical procedure in the surgical plan 1000.

In respect of the "Remove Tumour" surgical procedure, exemplary information is shown in FIG. 3. During the "Remove Tumour" surgical procedure, the surgical scene will contain various organs, body parts and tissue. This information will be provided by the surgeon during the surgical plan or will be obtained from a different database where other, similar, procedures have taken place. These are identified in the column "Anatomical Parts in Surgical Scene". Broadly, and as would be appreciated, the tumour, the stomach, spine and intestinal tract will be visible in the surgical scene. Additionally, parts of the patient's body will also be visible.

However, the tool mounted on the slave apparatus 90 will only need access to the tumour and the stomach in order to perform the surgical procedure of removing the tumour from the stomach. This is because the slave apparatus 90 will need to grip the tumour and cut into the stomach to remove the tumour. There is no need for the surgical device to access any of the spine, the intestinal tract or the body during this surgical procedure (unless there is an emergency situation). Therefore, the virtual barriers around the tumour and the stomach will be removed when an appropriate gesture is performed by the surgical device. However, the virtual barrier around the other exposed body parts should remain in place unless a further gesture or gestures (including voice commands) is/are performed indicating an emergency procedure.

Accordingly, the tumour and stomach are noted in the "Anatomical Parts to Access" column.

In order to perform this surgical procedure, forceps to grip and twist the tumour are required to be mounted onto the slave apparatus 90. In addition, a scalpel is required in order to cut the tumour from the stomach. Accordingly, forceps and scalpel are noted in the "surgical tool" column. Of course, other surgical tools such as a cauteriser (energy device) may be required, but these are not a pre-requisite to performing this part of the surgical procedure. Therefore, the cauteriser is not included in the "surgical tool" column. Of course, surgical tools that are not a pre-requisite to performing the surgical procedure may also be included in the data structure 1050. However, if these surgical tools are included in the data structure 1050, it is envisaged that they will be noted as optional to distinguish these optional surgical tools from the required surgical tools.

As noted above, in order to perform the "Remove Tumour" surgical procedure, the slave apparatus 90 will need to grip the tumour and rotate the tumour using the forceps. Typically, the forceps will need to rotate the tumour by 30° to 40°. Accordingly, the gesture the slave apparatus 90 holding the forceps will need to perform is a grip action and a rotation of 30° to 40° to show that the surgical device can have access to the tumour.

In addition, the surgical device controlled by the human surgeon will need to complete a diagonal cut of about 5 mm in order to cut the tumour from the stomach. Accordingly, the gesture the slave apparatus 90 holding the forceps will need to perform is a 5 mm diagonal cut somewhere in the surgical scene or somewhere on the virtual barrier to show that the surgical device can have access to the stomach. As noted above, the gesture performed by the surgical tool may be performed outside the surgical scene if required.

Once both gestures have been successfully completed, the virtual barrier around the tumour and the stomach will be removed. This allows the surgical device access to both the tumour and the stomach.

Of course it is possible that the virtual barrier around the tumour will be removed once the surgical device has performed the gesture with the forceps and then separately remove the virtual barrier around the stomach once the surgical device has performed the gesture with the scalpel. In other words, there is no requirement that both gestures must be successfully performed before either virtual barrier is removed.

Referring back to FIG. 3, although not shown for brevity, similar information would be included in the data structure 1050 for the repair patient surgical procedure in the surgical plan 1000.

The use of embodiments of the disclosure in the surgical procedure shown in FIG. 4A will now be described with references to FIGS. 2 to 9.

Figure 4A:
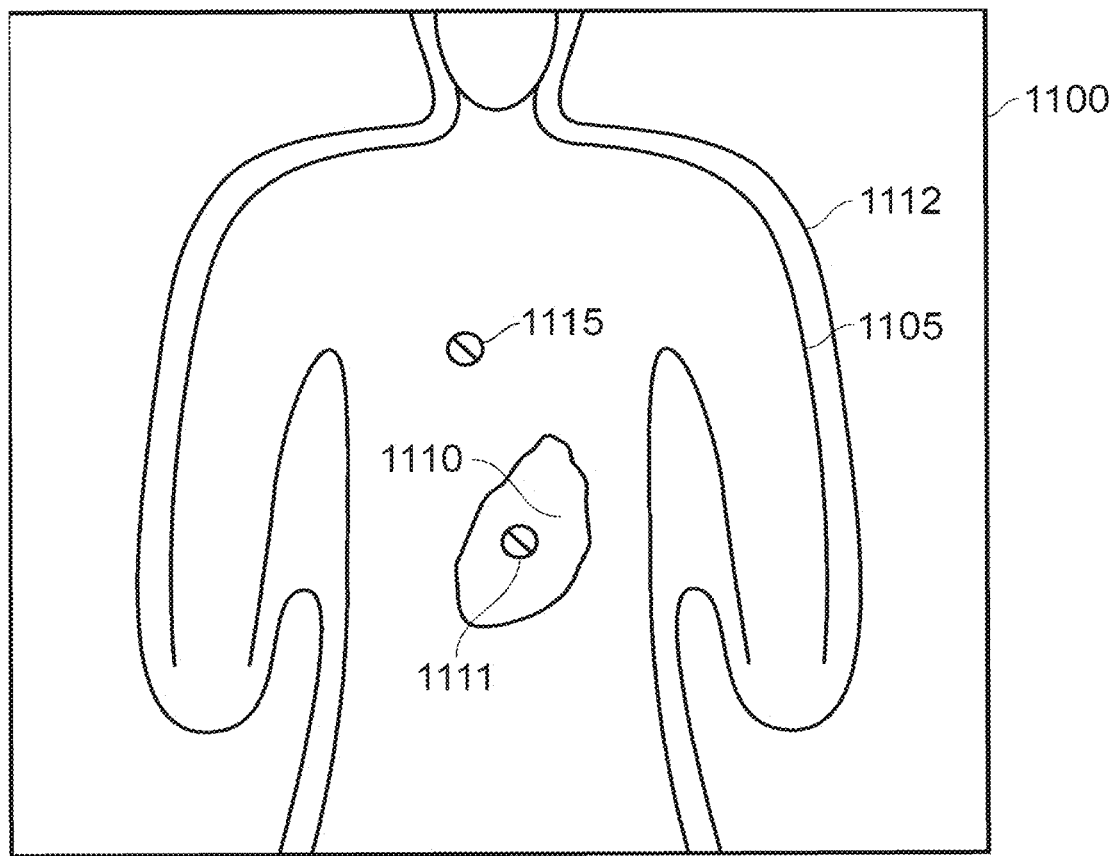
FIG. 4A shows a patient having virtual barriers for one step in the surgical procedure according to embodiments of the disclosure.

In FIG. 4A, an image 1100 of a patient 1105 is shown. The image 1100 is shown to the human surgeon controlling the slave apparatus 90. The image 1100 shows the surgical scene. Within the image 1100, the patient 1105 is shown. Additionally, two virtual barriers are shown. The virtual barriers define an area where access of the robot arm to part of the surgical site is to be restricted. These areas may be defined during the surgical plan. One embodiment explaining the generation of a virtual barrier is explained in WO2018/159328, the contents of which pertaining to the generation of virtual barriers (termed a "virtual plane" in this document) is hereby incorporated by reference.

In FIG. 4A, the first virtual barrier 1112 surrounds the entirety of the patient. The second virtual barrier 1110 surrounds the entirety of the patient's stomach. This means that the second virtual barrier 1110 is located within the first virtual barrier 1112. In other words, the second virtual barrier 1110 is a segment of the first virtual barrier 1112.

In order for the human surgeon to know the location of the virtual barrier and that a virtual barrier exists, a first icon 1115 is shown to identify the first virtual barrier 1112 and a second icon 1111 is shown to identify the second virtual barrier 1110. One or both of these icons may be shown in an image of the surgical scene displayed on a display viewed by the human surgeon, as Augmented Reality on a headset or glasses worn by the surgeon, or the icon(s) may be physically projected onto the real-life surgical scene.

Moreover, the boundary of the first virtual barrier 1112 and the second virtual barrier 1110 may be shown on the surgical scene in the same manner as described with reference to the first icon 1115 and second icon 1111. In other words, the first virtual barrier 1112 and/or the second virtual barrier 1110 may be displayed to the human surgeon using Augmented Reality or may be physically projected onto the patient undergoing surgery. The distance between the boundary of any virtual barrier and the anatomical part that is being encapsulated may be a predetermined amount. For example, the virtual barrier may be set at 2cm away from the surface of the anatomical part at all points. In other instances, the distance between the anatomical part and the surface may vary in dependence upon the criticality of the anatomical part. For example, the distance between a critical anatomical part (such as the heart) and the virtual barrier may be set at 5cm to reduce the risk of injury to that anatomical part. However, with less critical anatomical parts (such as skin) the virtual barrier may be set at 1cm away from the surface of the skin.

By showing boundary of the first virtual barrier 1112 and the second virtual barrier 1110 to the human surgeon, the human surgeon knows the areas of the surgical scene in which the tool mounted on the slave apparatus 90 is permitted and where the tool is not permitted. Moreover, by showing the first icon 1115 and the second icon 1111 to the human surgeon, the human surgeon knows that the boundaries define the first and second virtual barriers. In order to further improve the distinction between the first and second virtual barrier 1112 and 1110, the boundary may be provided in different colours, or may be drawn with different styles of lines (such as a dashed line and a dotted line), or may be numbered using different numbers or the like.

Figure 4B:
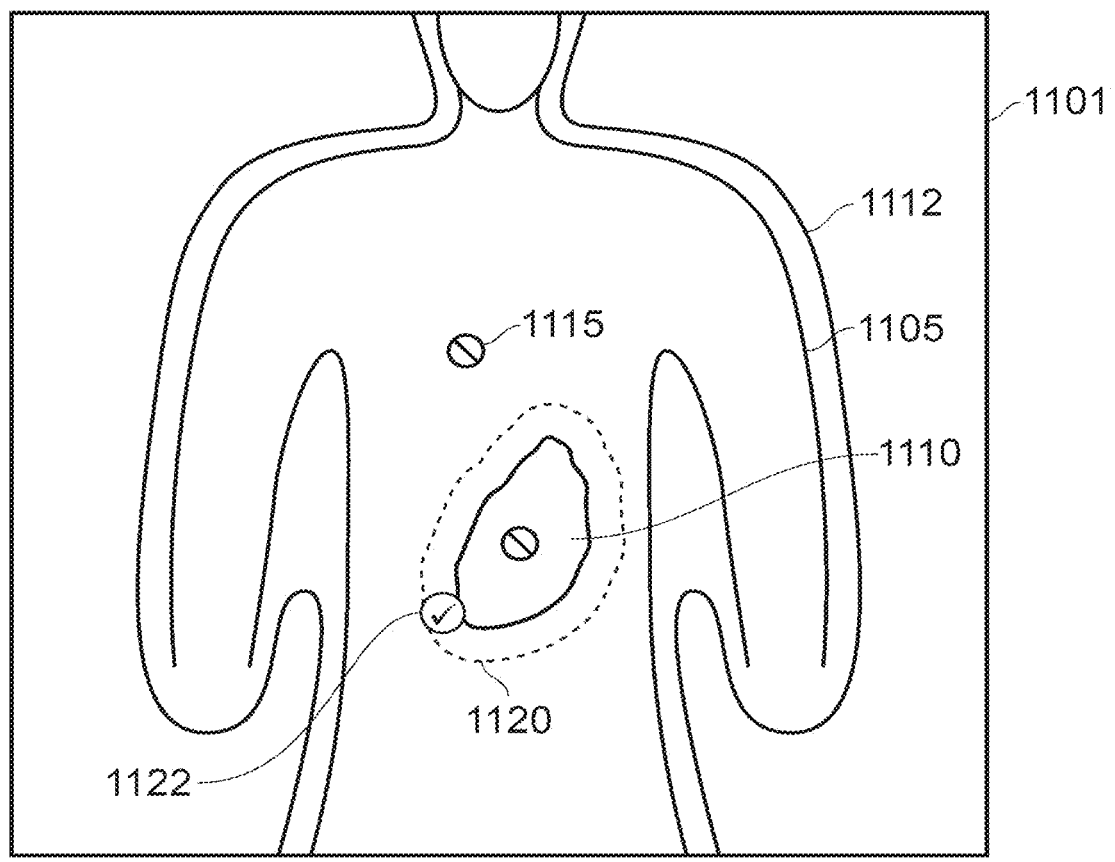
FIG. 4B shows a patient having virtual barriers for one step in the surgical procedure according to embodiments of the disclosure.

Referring to FIG. 4B, the surgical scene is shown without the presence of the second virtual barrier. In other words, the second virtual barrier has been removed. The mechanism to remove the second virtual barrier 1110 will be described with reference to FIG. 5A.

Once the second virtual barrier 1110 has been removed, the tool attached to the slave apparatus 90 is now permitted in the area defined by the dotted line 1120. This enables to the tool and the slave apparatus 90 (under the control of the human surgeon) to access the permitted area 1120. A permitted area icon 122 is shown within the boundary of the dotted line 1120. In this case the permitted icon 122 is a tick in a circle and whose colour may be selected to allow the human surgeon to quickly establish that the boundary line 1120 defines the permitted area. In the example of FIG. 4B, the permitted icon is a green colored check mark although any type of icon is envisaged.

Figure 5A:
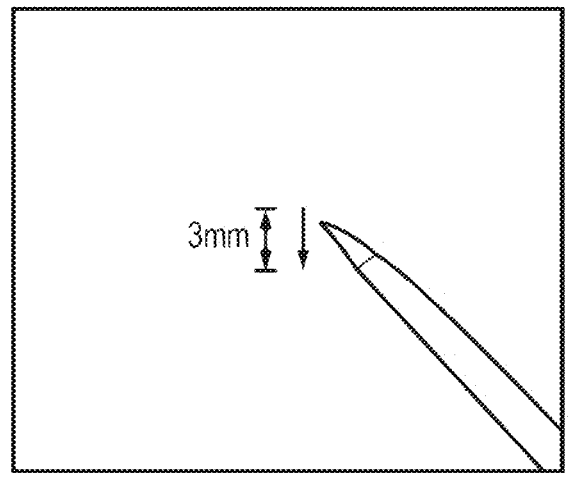
FIG. 5A shows various gestures required to unlock the virtual barriers according to embodiments of the disclosure.

Referring to FIG. 5A, and as noted above, in order to gain access to the stomach area (which is the "Anatomical Part in the Surgical Scene" column in data structure 1050 associated with the Incision Surgical Step), the human surgeon must pass a gesture test. This gesture test is a vertical movement downwards of 3 mm of the scalpel. This replicates the movement of the scalpel in order to perform an incision of the stomach. As noted above, the force sensor 91 and rotation angle sensor 93 within the slave apparatus 90 may be used to determine the depth of movement of the scalpel. Of course, the disclosure is not so limited and an image of the surgical site may be used to determine the movement of the scalpel.

Once the gesture test is passed, the second virtual barrier 1110 surrounding the stomach area 1120 is removed allowing the surgical tool attached to the slave apparatus 90 to access the stomach area 1120.

The slave apparatus 90 under the control of the human surgeon then performs the required steps of this part of the surgical procedure. After completion of this part of the surgical procedure, the control apparatus 79 determines that the surgical step has been completed. This may be determined in response to a command issued by the human surgeon (such as a voice command) or from the image of the surgical scene. For example, the surgical scene may include a new surgical tool being brought into view. This may mark the end of the current surgical step.

The control apparatus 79 then determines from the data structure 1050 that there are further surgical steps to be performed.

As noted in respect of FIG. 3, the next surgical step is the "Expose Stomach" step. The details of this step have been not included for brevity and so the next step that has been described in detail is the "Remove Tumour" surgical step. This is described with reference to FIGS. 6A, 6B and 7A and 7B and FIGS. 5B and 5C.

Figure 6A:
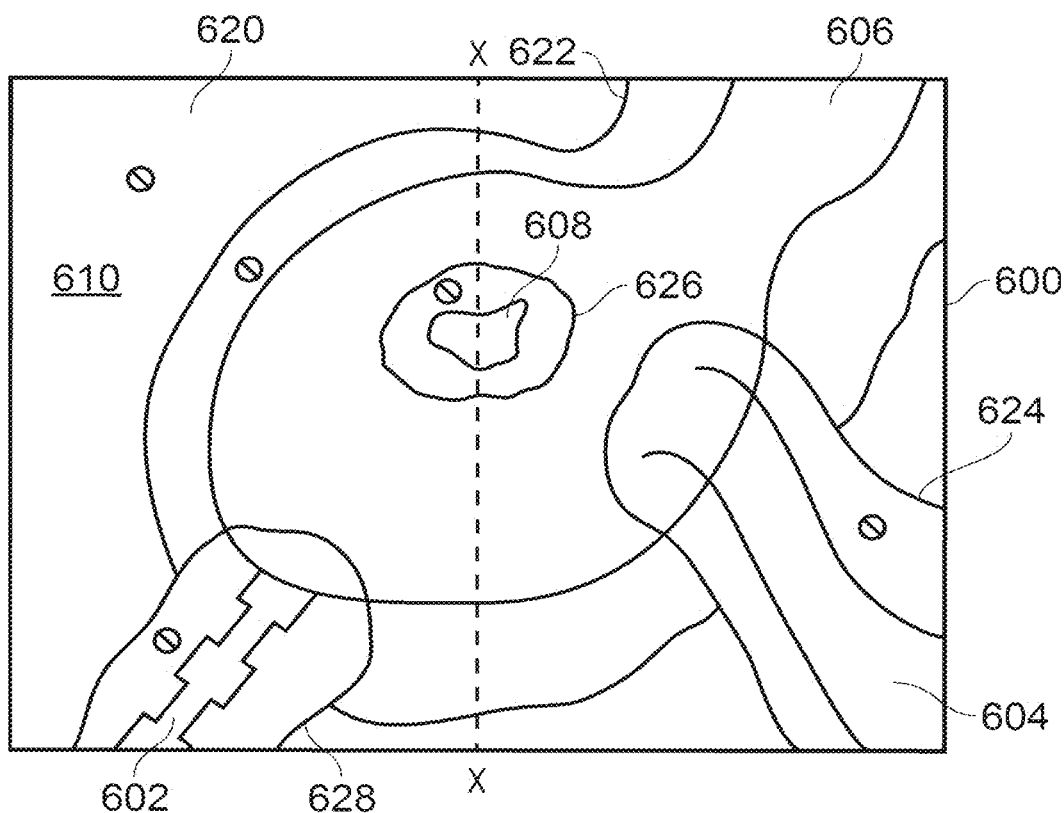
FIG. 6A shows a patient having virtual barriers for a second step in the surgical procedure according to embodiments of the disclosure.

Referring to FIG. 6A, once the stomach has been exposed, the surgical scene 600 will include various organs and tissue as defined in the "Anatomical Part in Surgical Scene" column of data structure 1050. For example, the spine 602, intestinal tract 604, stomach 606, tumour 608 and body 610 will be in the surgical scene 600.

As noted in the column "Anatomical Parts to Access" column, the surgical tool mounted on the slave apparatus 90 will need to access the stomach 606 and the tumour 608 during this surgical step.

However, in order to protect the patient, a third to seventh virtual barrier is provided protecting the various organs and tissue in the surgical scene 600. Specifically, a third virtual barrier 620 is provided to encapsulate and protect the body 610. Further, the fourth virtual barrier 622 is provided to encapsulate and protect the stomach 606; the fifth virtual barrier 624 is provided to encapsulate and protect the intestinal tract 604; the sixth virtual barrier 626 is provided to encapsulate and protect the tumour 608 and the seventh virtual barrier 628 is provided to encapsulate and protect the spine 602. The virtual barriers are generated in the manner described in WO2018/159328, the contents of which pertaining to the generation of virtual barriers (termed a "virtual plane" in this document) is hereby incorporated by reference.

Figure 6B:
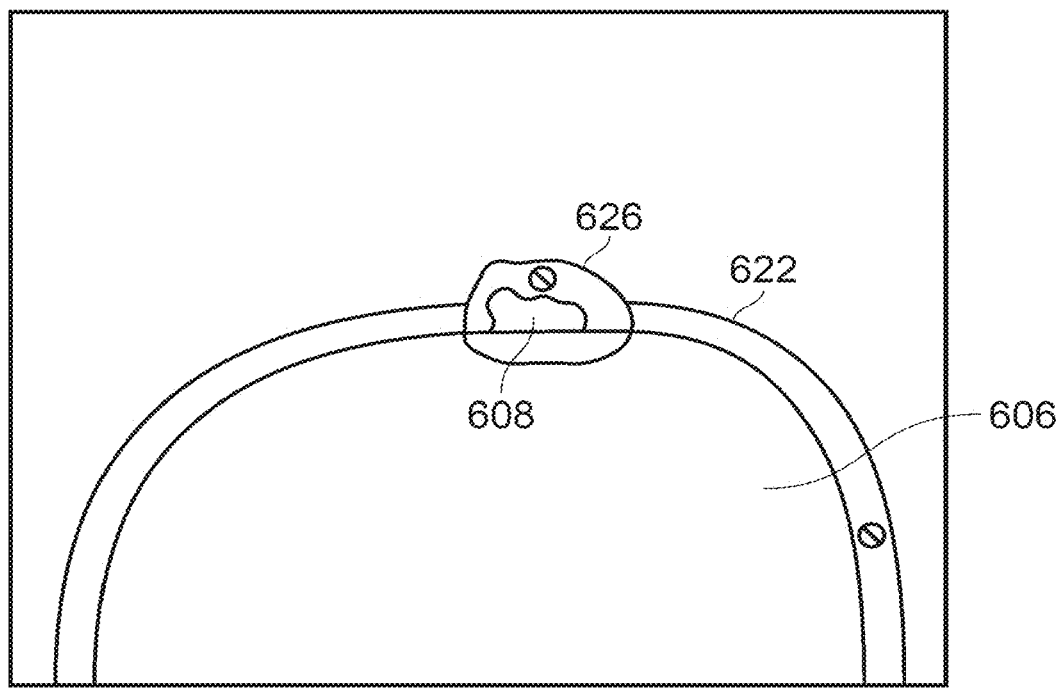
FIG. 6B shows a patient having virtual barriers for a second step in the surgical procedure according to embodiments of the disclosure.

Although the foregoing has shown the virtual barriers protecting a 2 dimensional space, the disclosure is not so limited. In FIG. 6B, a cross-sectional view along line X-X of FIG. 6A is shown. In particular, the stomach 606 and tumour 608 are shown. Moreover, the fourth virtual barrier 622 and the sixth virtual barrier 626 are shown. As will be appreciated by the skilled person, the depth of incision (as well as the location of the incision) is important during surgery. Therefore, the virtual barriers may include a depth limit. As noted above, the human surgeon is required to perform a 5 mm deep incision during the removal of the tumour step. Therefore, the depth of the sixth virtual barrier 626 is 5 mm below the tumour 608.

This will stop the scalpel cutting into the stomach 606 too deeply. In order to judge the depth of the incision, when contact is made between the scalpel and the tumour 626, a slight deflection in the tumour 626 at the incision point will be observed in the surgical scene. The rotation angle sensor 93 can then judge the depth of this incision. In the event that the depth of the incision will exceed the sixth virtual barrier, the motor 95 within the slave apparatus 90 will cease moving the scalpel vertically downward into the stomach.

Figure 5B:
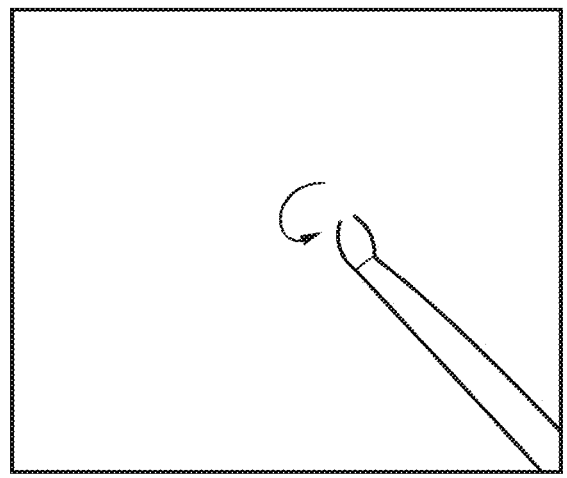
FIG. 5B shows various gestures required to unlock the virtual barriers according to embodiments of the disclosure.
Figure 5C:
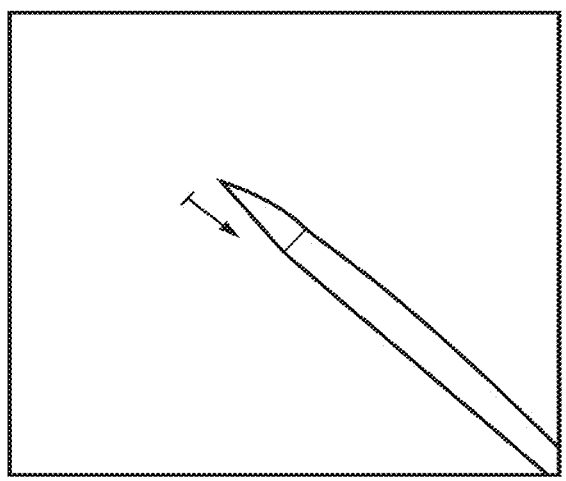
FIG. 5C shows various gestures required to unlock the virtual barriers according to embodiments of the disclosure.
Figure 7A:
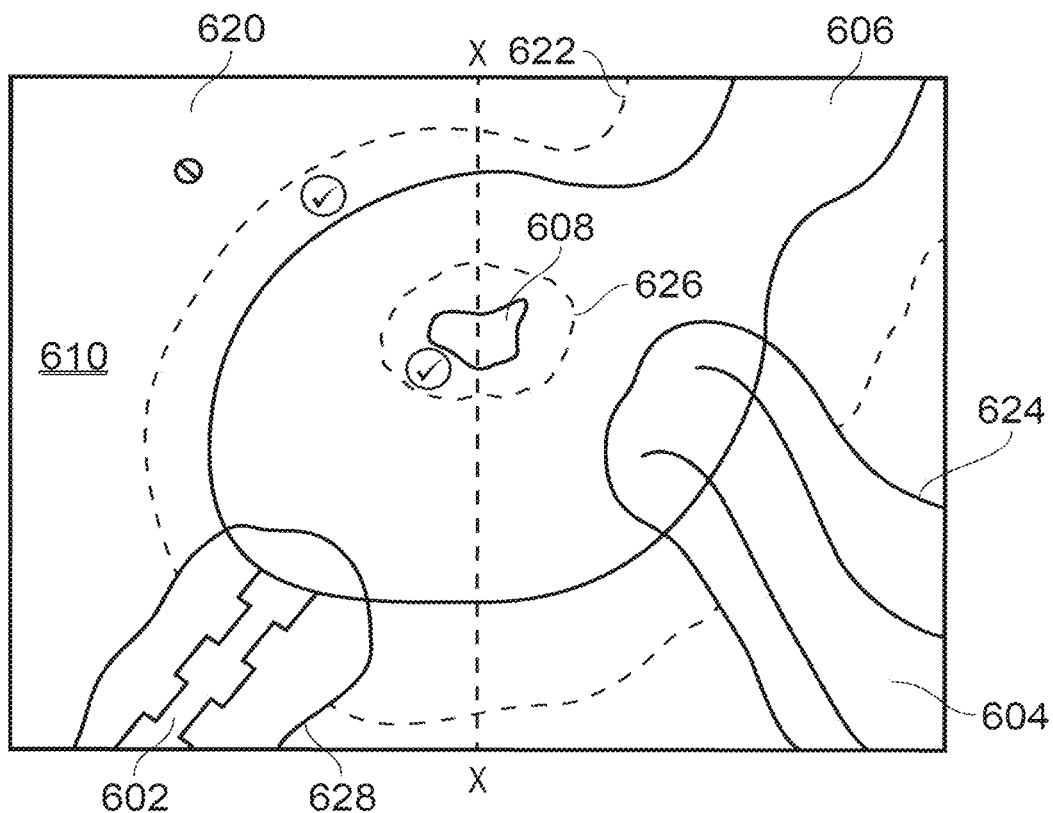
FIG. 7A shows a patient having virtual barriers for a second step in the surgical procedure according to embodiments of the disclosure.
Figure 7B:
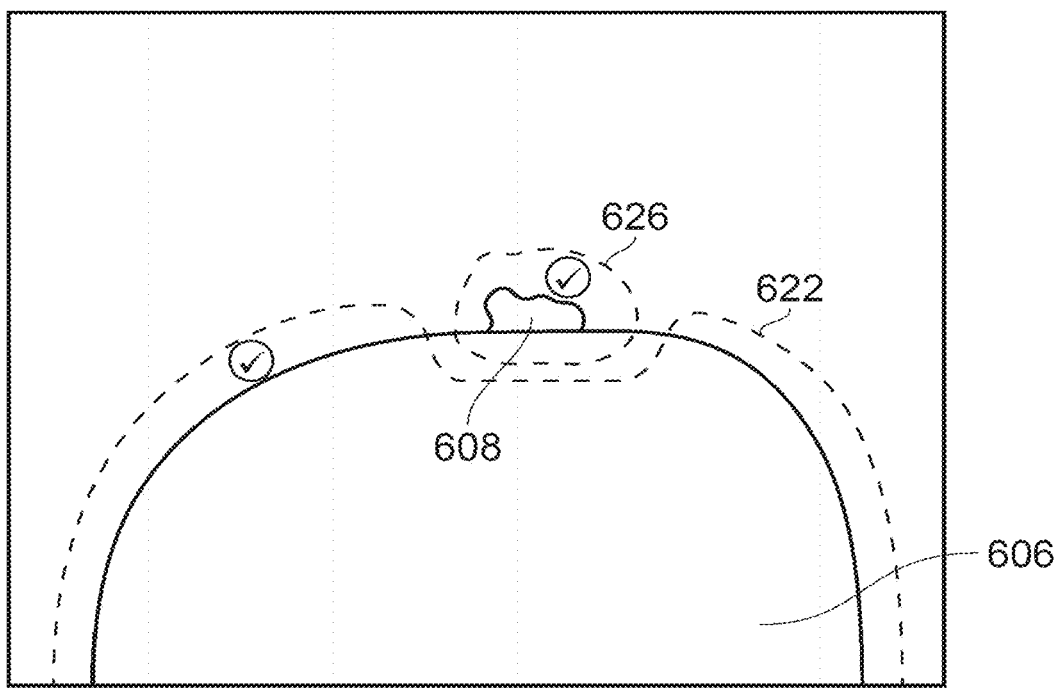
FIG. 7B shows a patient having virtual barriers for a second step in the surgical procedure according to embodiments of the disclosure.

Referring to FIG. 7A, the human surgeon will control the surgical tool attached to the slave apparatus 90 to perform certain gestures to remove the sixth virtual barrier 626 that encapsulates and protects the tumour 608 and the fourth virtual barrier 622 that encapsulates and protects the stomach 606. The gesture is noted in the "Gesture" column of the data structure 1050. In particular, the gesture to remove the sixth virtual barrier 626 around the tumour 608 is a grip of the forceps and a 40° rotation. This is illustrated in FIG. 5B. The gesture to remove the fourth virtual barrier 622 around the stomach 606 is a diagonal cut movement with 5 mm cutting depth. This is illustrated in FIG. 5C.

After the fourth virtual barrier 622 and the sixth virtual barrier 626 have been removed because the human surgeon has performed the requisite gesture, the line defining the fourth virtual barrier 622 and the sixth virtual barrier 626 is changed (for example to become a dashed line) and the icon is changed from the first icon to the second icon. This indicates to the human surgeon that the surgical tool may now enter the area defined by the fourth and sixth virtual barrier respectively.

Again, the control apparatus 79 determines whether there is a further surgical step. In this case, there is a final surgical step to be performed.

The next surgical step is the "Repair Patient" step. This will not be described in detail for brevity. However, at the end of this surgical step, no further surgical steps are noted in the data structure 1050 and so the surgery is complete.

Figure 8:
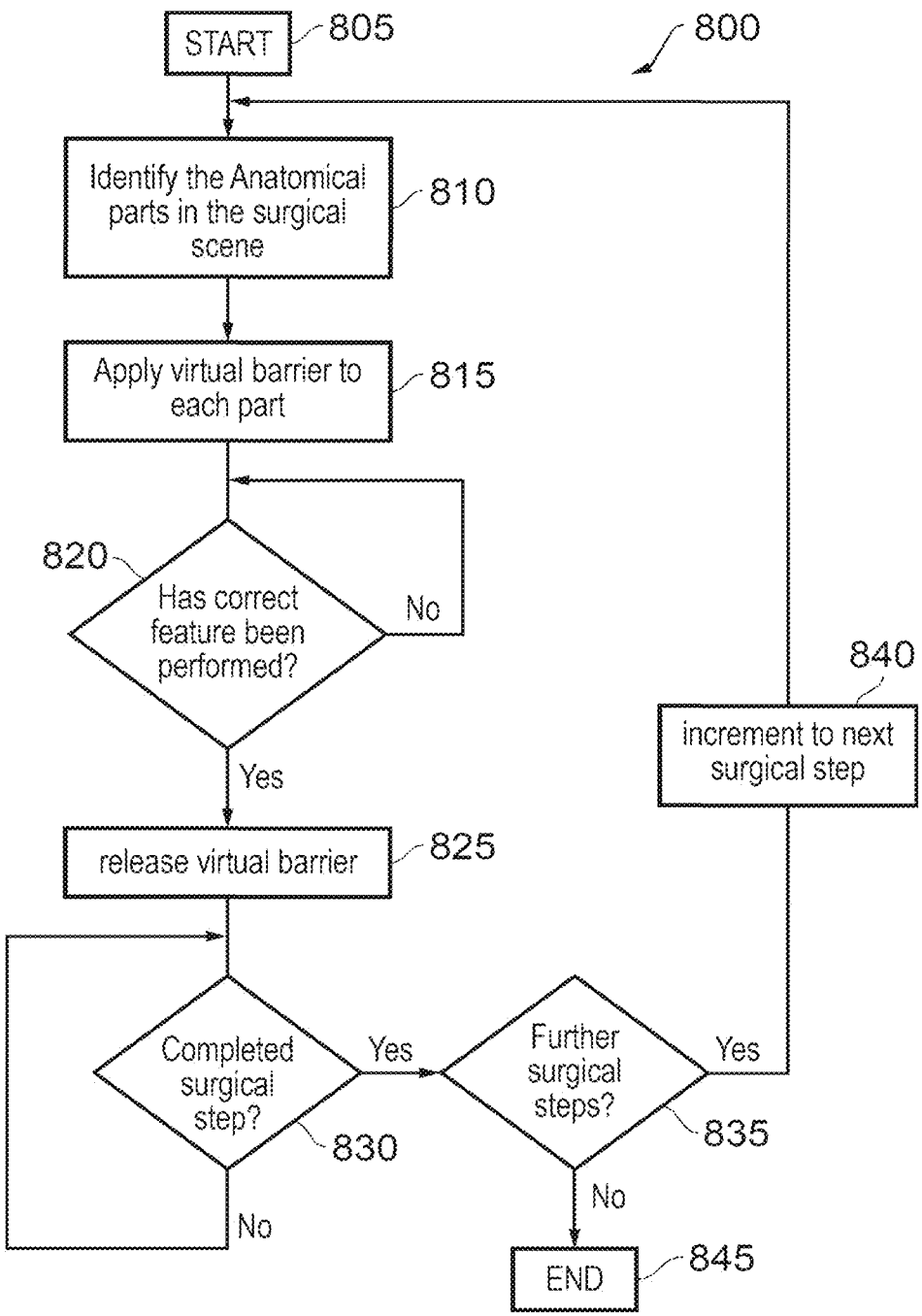
FIG. 8 shows a flow chart explaining a process performed by a control apparatus according to embodiments of the disclosure.

Referring to FIG. 8 a flow chart showing the process carried out by the control apparatus 79 is described. This process is carried out, in embodiments, by the processing circuitry 79A within the control apparatus 79. The processing circuitry 79A is a microprocessor or the like that operates under the control of computer software stored on storage 79B which may be located within the control apparatus 79 (as shown in FIG. 1) or may be located over a network to which the control apparatus 79 is connected.

The process 800 starts in step 805. The process moves onto step 810 where the anatomical parts in the surgical scene are identified. This may be achieved using image recognition or may require the human surgeon to identify the anatomical parts using an interface.

The process then moves to step 815 where a virtual barrier is applied around each anatomical part. The process then moves to step 820 where the gesture of the surgeon is checked to see if the surgeon has passed the gesture check. In other words, the surgeon performs the gesture to release the virtual barrier and the gesture performed by the surgeon is compared with the gesture stored in data structure 1050. If the surgeon has not passed the gesture check, the "no" path is followed to the start of the step. Otherwise, the "yes" path is followed to step 825.

In step 825, the virtual barrier for which the surgeon has passed the gesture test is removed.

The process then moves to step 830 where a check is performed to determine whether the surgical step has been completed. As noted above, the human surgeon may issue a voice command, for example, indicating that this step in the surgical procedure is completed. In the event that the surgical step has not been completed, the "no" path is followed to the beginning of step 830. However, where the surgical step has been completed, the "yes" path is followed to step 835.

In step 835, the control apparatus 79 determines whether further surgical steps are required in order to complete the surgical procedure. In the event that further surgical steps are required, the "yes" path is followed to step 840, where the next surgical step in the data structure 1050 defining the surgical procedure is accessed. The process then returns to step 810.

On the other hand, if in step 835 no further surgical steps are required, the "no" path is followed to step 845 where the process 800 ends.

Although the foregoing has explained various depths and angles to be performed during the gesture test, the skilled person will appreciate that there are tolerances associated with these gestures. For example, although the incision requires a depth of 3 mm, the gesture may be passed if the surgeon performs a gesture of 4 mm instead of 3 mm. In this instance, it is possible that the tolerance may vary depending on the accuracy required and the risk of injury to the patient if a mistake in the surgical procedure is performed. For example, if the surgeon performs a 4 mm incision when cutting the stomach, there is little risk to the patient. However, if the surgeon performs an incision that is too deep on an artery, the patient may die. Therefore, the tolerance level for lower risk procedures or surgical sites may be higher than for high risk procedures of surgical sites.

The tolerance level may also be determined in accordance with the danger attributed to the surgical tool. For example, a tolerance attributed to a scalpel may be less than that attributed to a pair of forceps because an error with a scalpel tends to lead to a higher risk for a patient than an error with a pair of forceps.

Moreover, the tolerance levels may vary depending upon the well-being of the patient. In the event that a surgeon must perform a surgical step quickly due to the patient being in a critical condition, the tolerance level to the accuracy of the gestures may be reduced.

In addition, the speed at which the gesture has been performed may be determined. This speed may be compared with an acceptable speed and the virtual barrier may only be removed if the gestures have been performed at a speed within the acceptable range. In addition, the number of attempts made by the surgeon before removal of the virtual barrier may be counted. In the event that the number of attempts is above a threshold or the error associated with the gesture at failure is above a predetermined amount, the surgeon may be identified for additional training on that surgical step.

Although the foregoing has described anatomical parts as being tissue or organs, the disclosure is not so limited. An anatomical part may include a subdivision of an organ, for example, a first or second liver lobe.

As explained above, one surgical scene may include one or more virtual barriers which need removal. In the case of a plurality of virtual barriers, the virtual barriers may need to be removed in an order defined in the surgical procedure plan set out in the data structure 1050. In this case, the virtual barriers may be annotated with a sequence of numbers or letters identifying the order in which the virtual barriers must be removed. This will assist the surgeon in performing the surgery.

Although the foregoing has been described with reference to a "master-slave" robotic system, the disclosure is not so limited. In some instances, the surgical robot may work independently of the human surgeon with the human surgeon being present in a supervisory capacity. Moreover, with endoscopy or laparoscopy, the scopist may be a robot with a human surgeon directing the robot. In embodiments, the robotic system may be a multi-robots surgical system where a main surgeon will use a robotic surgeon and an assistant surgeon will teleoperate assistive robotic arms. The robotic system may be a solo-surgery system which consists of a pair of co-operating and autonomous robotic arms holding the surgical instruments. In this case, the human surgeon may use a master-slave arrangement.

Although the foregoing has been explained with regard to removing a tumour from a stomach, the disclosure is in no way limited to this. Example gestures and virtual barriers for different scenarios will now be described.
Organ: skin/muscle wall
Surgical tool: Scalpel
Surgical process: initial incision A virtual barrier over an initial incision site may have an unlockable section which is subdivided from the rest of the barrier. An incision at this site requires an approach from the left side relative to the patient for further actions to be performed in the best way. The unlock gesture may therefore consist of a movement of the robotic arm joints without moving the scalpel from a right orientation to the left, such that the available ranges of motility are more suitable for the incision.
Organ: skin/connective tissue/other
Surgical tool: suture needle and thread
Surgical process: suture A tissue cut line which is due to be sutured closed, is protected by a plurality of small virtual barrier sections which protect different length sections of the tissue boundary.

The gesture required for each section may be a suture action, correctly performed on the previous section. Therefore, the virtual barrier opening would move progressively along the line of the cut as the suturing is performed by the surgeon controlled robot. Also, consequently, if there is a mistake in the suturing process, this may be prevented from propagating as the next section will not be unlocked.
Organ: Vein
Surgical tool: Scalpel
Surgical process: Vein transposition In a scenario where a vein must be excised for a transposition procedure, the exposed vein may be protected by a virtual barrier section which covers the entire length of the exposed vein and 5 mm either side. This section may have an associated gesture where the surgeon may perform:

1) A movement of the scalpel blade in a curved motion, keeping the scalpel blade face in the direction of motion. The curve degree is chosen to match the maximum curvature along the length of the vein which must be cut open.

2) Multiple linear movements which represent 'skip incisions' above the surface of the vein down its length, as this is a recognized best practice for the procedure and detected vein parameters.

In performing the gesture, the system recognizes that the operator has sufficient skill with the surgical platform, and unlocks the section.
Organ: tendon
Surgical tool: curved forceps
Surgical process: tendon clamping In a scenario where a tendon must be seized or clamped during a procedure, a small section of the exposed tendon where the clamp should be placed is locked by a virtual barrier. Surrounding areas of tendon may optionally be protected by a barrier that does not unlock.

The unlock gesture may require a specific tool type to be completed, such as curved forceps rather than a straight tool. In this case the gesture may include movement of the tool tip in a curved arc, without the tool body deviating from the curved line that the tool tip followed, which can only be achieved by a suitable curved tool.

Figure 9:
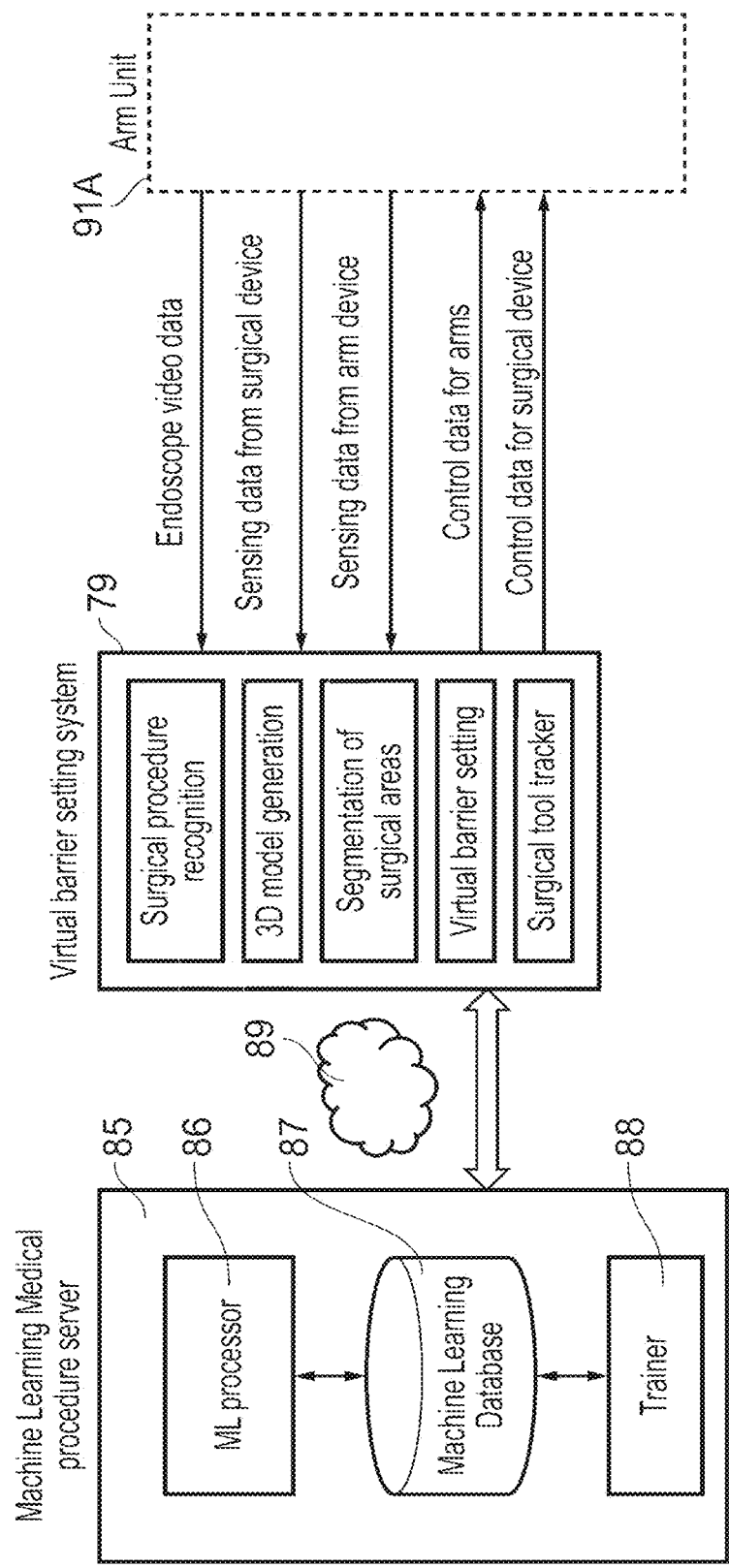
FIG. 9 shows the virtual barrier setting system 79 of FIG. 1 in more detail.

FIG. 9 shows the virtual barrier setting system 79 of FIG. 1 in more detail. The arm unit 91A provides image data to the virtual barrier setting system 79. In this case, the arm unit 91A provides endoscopic image data to the virtual barrier setting system 79. In addition, sensing data from the surgical device are provided to the virtual barrier setting system 79. In the example where the surgical device is an endoscope, the sensing data may be the focus length of the image and the zoom settings of the endoscope. Of course, the disclosure is not so limited and where the surgical device is, for example, a cauterizer, the sensing data may include the position of the end effector, or the energy being provided by the cauteriser to the wound within the surgical scene.

In addition, sensing data from the arm unit 91A is provided to the virtual barrier setting system 79. This sensing data may include the position of the arm unit 91A within the surgical scene or the control signals being applied to the actuators 97 within the arm unit 91A or the like. This sensing data allows the virtual barrier setting system 79 to determine the position of the arm unit 91A so that the virtual barrier setting system 79 can stop the arm unit 91A from breaching a virtual barrier.

As noted in respect of FIG. 1, in the event that a virtual barrier will be breached, control data is sent to the arm unit and, if necessary, the surgical device attached to the arm unit to stop the virtual barrier being breached.

As will be apparent from the description above, the virtual barrier setting system 79 performs several functions.

Firstly, the virtual barrier setting system 79 performs surgical procedure recognition that identifies the surgical procedure being carried out. This information may be provided by a surgeon or an administrator. Further this information may be provided by a facilities management system that reserves operating theatres and schedules surgeon availability and the like.

The virtual barrier setting system 79 also performs 3D model generation that builds a 3D model of the surgical site. This allows the virtual barriers to have a 3 dimensional shape as explained above. This further protects the patient during surgery.

In order to define the virtual barriers, as noted above, it is sometimes useful to segment the surgical site into two or more areas. These areas may each have one or more virtual barriers applied. For example, the surgical site may be segmented into areas including one or more internal organ or the like.

The virtual barriers may be set by the virtual barrier setting function that analyses the surgical procedure, identifies the steps carried out in such a procedure, identifies the risks associated with each step in the procedure and then defines the virtual barriers to mitigate those risks.

Finally, the surgical tool tracker function tracks the position of the surgical tool within the surgical site. This allows the virtual barrier setting system 79 to compare the position of the surgical tool with the virtual barrier and in the event that the surgical tool or arm unit will breach the virtual barrier, the virtual barrier setting system 79 will issue an instruction to stop the surgical tool or arm unit.

Although the functions within the virtual barrier setting system 79 may be defined by a surgeon or administrator as noted above, the disclosure is not so limited. For example, the virtual barrier setting system 79 may communicate with a machine learning server 85 over a network 89.

In the machine learning server 85, there is provided a machine learning processor 86 that is processing circuitry configured to perform machine learning. The machine learning processor 86 may be controlled by software which comprises computer readable instructions.

The machine learning server 85 also includes a machine learning database 87 and a trainer 88. The trainer 88 is used to allow the virtual barrier setting system 79 to recognise the current step in the surgical procedure from many images of previous surgical sites. In other words, the trainer 88 analyses many images of known surgical sites and their respective step in a surgical procedure and stores the pertinent information in the machine learning database 87 so that the virtual barrier setting system 79 may automatically recognise the current step from the currently captured image.

Further, the trainer 88 is used to allow the virtual barrier setting system 79 to recognise the different areas within the surgical site from the currently captured image. For example, the trainer 88 analyses many images of various organs and areas within a surgical site and stores the pertinent information within the machine learning database 87. The machine learning database 87 then provides the pertinent information to the virtual barrier setting system 79 so that the virtual barrier setting system 79 may automatically identify the different area from the current captured image.

Numerous modifications and variations of the present disclosure are possible in light of the above teachings. It is therefore to be understood that within the scope of the appended claims, the disclosure may be practiced otherwise than as specifically described herein.

In so far as embodiments of the disclosure have been described as being implemented, at least in part, by software-controlled data processing apparatus, it will be appreciated that a non-transitory machine-readable medium carrying such software, such as an optical disk, a magnetic disk, semiconductor memory or the like, is also considered to represent an embodiment of the present disclosure.

It will be appreciated that the above description for clarity has described embodiments with reference to different functional units, circuitry and/or processors. However, it will be apparent that any suitable distribution of functionality between different functional units, circuitry and/or processors may be used without detracting from the embodiments.

Described embodiments may be implemented in any suitable form including hardware, software, firmware or any combination of these. Described embodiments may optionally be implemented at least partly as computer software running on one or more data processors and/or digital signal processors. The elements and components of any embodiment may be physically, functionally and logically implemented in any suitable way. Indeed the functionality may be implemented in a single unit, in a plurality of units or as part of other functional units. As such, the disclosed embodiments may be implemented in a single unit or may be physically and functionally distributed between different units, circuitry and/or processors.

Although the present disclosure has been described in connection with some embodiments, it is not intended to be limited to the specific form set forth herein. Additionally, although a feature may appear to be described in connection with particular embodiments, one skilled in the art would recognize that various features of the described embodiments may be combined in any manner suitable to implement the technique.

Embodiments of the present technique can generally described by the following numbered clauses:

(1)
A robotic arm system for surgery, including:
processing circuitry configured to: apply a virtual barrier preventing a human controlled surgical device from entering an area within a surgical scene; and release the virtual barrier in response to a gesture.

(2)
A system according to clause 1, wherein the gesture is performed by the human controlled surgical device.

(3)
A system according to clause 1, wherein the gesture is the opening and/or closing of the human controlled surgical device.

(4)
A system according to clause 1, wherein the gesture is a movement of a pattern on the virtual barrier.

(5)
A system according to clause 4, wherein the pattern is a plurality of taps on the virtual barrier.

(6)

A system according to clause 4, wherein the pattern is a movement of a trajectory across the surface of the virtual wall.

(7)

A system according to clause 1, wherein the gesture is selected based on the surgical procedure next being performed by the human controlled surgical device.

(8)

A system according to clause 7, wherein the gesture is selected based on the starting position of the human controlled surgical device of the surgical procedure next being performed.

(9)

A system according to clause 8, wherein the surgical procedure is one of cautery, ligature, extraction or puncture.

(10)

A system according to clause 4, wherein the gesture pattern is related to a particular structure located in the surgical site protected by the virtual barrier.

(11)

A system according to clause 1, wherein the processing circuitry is configured to: remove the virtual barrier in dependence upon the type of the human controlled surgical device.

(12)

A system according to clause 1, wherein an area of the surgical site defined by the virtual barrier is dependent upon the type of the human controlled surgical device.

(13)

A system according to clause 1, wherein the virtual barrier defines an area around an organ within the surgical scene.

(14)

A system according to clause 1, wherein the gesture is determined based on the urgency with which the area should be accessed.

(15)

A system according to clause 14, wherein the urgency is determined by the condition of the patient.

(16)

A system according to clause 1, including a user interface configured to receive an input from the human surgeon and the gesture is performed on the user interface.

(17)

A system according to clause 1, including a sensor configured to recognise the surgical site and wherein the processing circuitry is configured to define a plurality of areas within the surgical scene based on the recognized surgical site.

(18)

A system according to clause 17, wherein the sensor is one of an image sensor, a time of flight sensor or a multispectral sensor.

(19)

A system according to either one of clause 17 or 18, wherein the plurality of areas is defined according to the anatomical structure located in each area.

(20)

A system according to clause 19, wherein the anatomical structure is one of bone, tissue or artery.

(21)

A robotic arm system for surgery, including:

control processing circuitry configured to define a plurality of virtual barriers that prevent a contact of a surgical tool to a particular area within a surgical site, and to restrict the movement of the arm using the plurality of virtual barriers; and an interface configured to receive an input provided by a user to release at least one of the plurality of virtual barriers, wherein the respective virtual barrier is released in response to different types of input provided by the user.

(22)

A method of operating a robotic arm system for surgery, the method including:

applying a virtual barrier preventing a human controlled surgical device from entering an area within a surgical scene; and releasing the virtual barrier in response to a gesture.

(23)

A method according to clause 22, wherein the gesture is performed by the human controlled surgical device.

(24)

A method according to clause 22, wherein the gesture is the opening and/or closing of the human controlled surgical device.

(25)

A method according to clause 22, wherein the gesture is a movement of a pattern on the virtual barrier.

(26)

A method according to clause 25, wherein the pattern is a plurality of taps on the virtual barrier.

(27)

A method according to clause 25, wherein the pattern is a movement of a trajectory across the surface of the virtual wall.

(28)

A method according to any one of clauses 22 to 27, wherein the gesture is selected based on the surgical procedure next being performed by the human controlled surgical device.

(29)

A method according to clause 28, wherein the gesture is selected based on the starting position of the human controlled surgical device of the surgical procedure next being performed.

(30)

A method according to clause 29, wherein the surgical procedure is one of cautery, ligature, extraction or puncture.

(31)

A method according to clause 25, wherein the gesture pattern is related to a particular structure located in the surgical site protected by the virtual barrier.

(32)

A method according to clause 22, including: removing the virtual barrier in dependence upon the type of the human controlled surgical device.

(33)

A method according to clause 22, wherein an area of the surgical site defined by the virtual barrier is dependent upon the type of the human controlled surgical device.

(34)

A method according to clause 22, wherein the virtual barrier defines an area around an organ within the surgical scene.

(35)

A method according to clause 22, wherein the gesture is determined based on the urgency with which the area should be accessed.

(36)

A method according to clause 35, wherein the urgency is determined by the condition of the patient.

(37)

A method according to clause 22, including a user interface configured to receive an input from the human surgeon and the gesture is performed on the user interface.

(38)

A method according to clause 22, including recognizing the surgical site and wherein the processing circuitry is configured to define a plurality of areas within the surgical scene based on the recognized surgical site.

(39)

A method according to clause 38, wherein the recognizing step is performed by one of an image sensor, a time of flight sensor or a multispectral sensor.

(40)

A method according to clause 38, wherein the plurality of areas is defined according to the anatomical structure located in each area.

(41)

A method according to clause 40, wherein the anatomical structure is one of bone, tissue or artery.

(42)

A method of operating a robotic arm system for surgery, the method including: defining a plurality of virtual barriers that prevent a contact of a surgical tool to a particular area within a surgical site, and to restrict the movement of the arm using the plurality of virtual barriers; and receiving an input provided by a user to release at least one of the plurality of virtual barriers, wherein the respective virtual barrier is released in response to different types of input provided by the user.

(43)

A computer program product comprising computer readable code which, when loaded onto a computer, configures the computer to perform a method according to clause 22.

The invention claimed is:

1. A robotic arm system for surgery, comprising:
processing circuitry configured to
apply a virtual barrier that prevents a human controlled surgical device from entering an area within a surgical scene and to restrict movement of a robotic arm holding a surgical device, and
on condition that the surgical device held by the robotic arm corresponds to a surgical device to perform a next surgical procedure, release the virtual barrier in response to a gesture, wherein the gesture is selected based on a starting position of the human controlled surgical device of the next surgical procedure.

2. A system according to claim 1, wherein the surgical procedure is one of cautery, ligature, extraction or puncture.

3. A system according to claim 2, wherein the gesture is related to a particular structure located in a surgical site protected by the virtual barrier.

4. A system according to claim 2, wherein an area of the surgical site defined by the virtual barrier is dependent upon the type of the human controlled surgical device.

5. A system according to claim 2, wherein the virtual barrier defines an area around an organ within the surgical scene.

6. A system according to claim 2, wherein the gesture is determined based on the urgency with which the area should be accessed.

7. A system according to claim 6, wherein the urgency is determined by the condition of the patient.

8. A system according to claim 2, further comprising a user interface configured to receive an input from the user and the gesture is performed on the user interface.

9. A system according to claim 2, further comprising a sensor configured to recognize the surgical site and wherein the processing circuitry is configured to define a plurality of areas within the surgical scene based on the recognized surgical site.

10. A system according to claim 9, wherein the sensor is one of an image sensor, a time of flight sensor or a multispectral sensor.

11. A method of operating a robotic arm system for surgery, the method including:
applying a virtual barrier preventing a human controlled surgical device from entering an area within a surgical scene and restricting movement of a robotic arm holding a surgical device; and
on condition that the surgical device held by the robotic arm corresponds to a surgical device to perform a next surgical procedure, releasing the virtual barrier in response to a gesture, wherein the gesture is selected based on a starting position of the human controlled surgical device of the next surgical procedure.

* * * * *